(12) United States Patent
Jeon et al.

(10) Patent No.: US 7,310,542 B2
(45) Date of Patent: Dec. 18, 2007

(54) NON-INVASIVE BODY COMPONENT CONCENTRATION MEASURING APPARATUS AND METHOD OF NONINVASIVELY MEASURING A CONCENTRATION OF A BODY COMPONENT USING THE SAME

(75) Inventors: Kye-jin Jeon, Suwon-si (KR); Jong-youn Lee, Yongin-si (KR); In-duk Hwang, Suwon-si (KR); Kun-kook Park, Yongin-si (KR); Hye-jeong Kim, Yongin-si (KR); Hye-jin Jung, Seoul (KR); Eun-young Choe, Pohang-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 0 days.

(21) Appl. No.: 11/038,023

(22) Filed: Jan. 21, 2005

(65) Prior Publication Data

US 2005/0159658 A1  Jul. 21, 2005

(30) Foreign Application Priority Data

Jan. 20, 2004  (KR) ............... 10-2004-0004407

(51) Int. Cl.
*A61B 5/00* (2006.01)
(52) U.S. Cl. .................... 600/344; 600/309
(58) Field of Classification Search ........... 600/310, 600/322, 334, 335
See application file for complete search history.

(56) References Cited

U.S. PATENT DOCUMENTS 5,183,042 A * 2/1993 Harjunmaa et al. ......... 600/309
5,676,139 A * 10/1997 Goldberger et al. ........ 600/310
6,101,405 A * 8/2000 Yasuda et al. .............. 600/310
6,222,189 B1 4/2001 Misner et al. ........... 250/341.1
6,241,663 B1 6/2001 Wu et al. ................... 600/310
6,278,889 B1 8/2001 Robinson ................... 600/322
6,285,894 B1* 9/2001 Oppelt et al. .............. 600/322
6,309,884 B1 10/2001 Cooper et al. ............... 436/14

FOREIGN PATENT DOCUMENTS

| JP | 11-216131 | 8/1999 |
|---|---|---|
| KR | 2001-0067120 | 7/2001 |
| KR | 2002-0055364 | 7/2002 |

OTHER PUBLICATIONS

Marbach, Appln Spectroscopy 47, No. 7 pp. 875-881 (1993) "Noninvasive Blood Glucose Assay by Near Infrared Diffuse Reflectance Spectroscopy of the Human Inner Lip".

* cited by examiner

*Primary Examiner*—Eric F. Winakur
*Assistant Examiner*—Etsub D Berhanu
(74) *Attorney, Agent, or Firm*—Lee & Morse, P.C.

(57) ABSTRACT

In a non-invasive body component measuring apparatus for measuring a concentration of a body component in a measuring portion of a living body, and a method of non-invasively measuring the concentration of the body component, the non-invasive body component measuring apparatus includes a light source unit for generating light of a predetermined wavelength and for applying the light onto the measuring portion, a detection unit for detecting light reflected or transmitted by the measuring portion and for converting the detected light into an electrical signal, a signal processing unit for processing the electrical signal, and a body-apparatus interface unit for fixing a periphery of the measuring portion during measurement.

19 Claims, 10 Drawing Sheets

NON-INVASIVE BODY COMPONENT CONCENTRATION MEASURING APPARATUS AND METHOD OF NONINVASIVELY MEASURING A CONCENTRATION OF A BODY COMPONENT USING THE SAME

BACKGROUND OF THE INVENTION

1. Field of the Invention

The present invention relates to a method and apparatus for performing a non-invasive measurement of a concentration of a body component. More specifically, the present invention relates to a non-invasive body component concentration measuring apparatus and method of noninvasively measuring a concentration of a body component using a difference absorption spectrum corresponding to a quantity of interstitial fluid varied by adjusting a thickness of a specific soft tissue of a sample.

2. Description of the Related Art

Presently, about 5% of the human population suffers from diabetes, and this percentage is increasing. Diabetes is a chronic disease for which there is no complete cure, and requires a lifetime of attention and/or treatment, including self care by a patient.

Self care requires that a diabetic himself must measure his blood glucose from blood collected from a fingertip two to five times a day using a home blood glucose meter. The diabetic then records the measured blood glucose in a diabetic diary, and must adjust intake of food, physical activity, and/or use of medication or insulin depending on the measured results. The recorded blood glucose can be maintained by the diabetic and provided to a doctor during medical treatment.

Unfortunately for diabetics, pain and infections may be caused by frequent collection of blood. Thus, daily measurement of blood glucose imposes a significant burden on a diabetic. Therefore, studies of measuring blood glucose without collecting blood have been conducted. For example, research has been conducted into applying harmless light onto a part of a human body and detecting the light having reacted with the human body to measure the blood glucose of the human body.

By means of near-infrared spectroscopy employing a multi-variation statistical analysis, glucose in complicated biological media or various reacting mixtures can be selectively analyzed, which is one of the above-mentioned studies. Nevertheless, the technology of extracting glucose data from near-infrared spectra non-invasively measured from the human body still has significant technical problems that remain to be solved.

More specifically, several research reports have reported successful measurements of blood glucose, but in these reports, signal-to-noise ratios of the spectra are low, specificity of the blood glucose is low, and reproducibility of the measured signals is low.

In order to solve the above problems, several conventional methods of measuring blood glucose through absorbance analysis using a glucose overtone band and a combination band in a near-infrared area to develop a bloodless blood glucose meter have been suggested. Each of these conventional methods, however, suffer from disadvantages such as significant estimation error due to variations in conditions during measurements, difficulty in estimating a concentration of glucose in particular, and difficulty regarding reproducibility.

SUMMARY OF THE INVENTION

The present invention is therefore directed to a non-invasive body component measuring apparatus and method, which substantially overcome one or more of the problems due to the limitations and disadvantages of the related art.

It is a feature of an embodiment of the present invention to provide a non-invasive body component measuring apparatus and method that are capable of measuring a concentration of a body component, e.g., blood glucose, without requiring a physical collection of a blood sample.

It is another feature of an embodiment of the present invention to provide a non-invasive body component measuring apparatus and method that use a difference absorption spectrum corresponding to a quantity of interstitial fluid varied by adjusting a thickness of a specific soft tissue of a sample, i.e., a measuring portion, while stably maintaining cellular tissues.

At least one of the above features and other advantages may be provided by a non-invasive body component measuring apparatus for measuring a concentration of a body component in a measuring portion of a living body, the apparatus including a light source unit for generating light of a predetermined wavelength and for applying the light onto the measuring portion, a detection unit for detecting light reflected or transmitted by the measuring portion and for converting the detected light into an electrical signal, a signal processing unit for processing the electrical signal, and a body-apparatus interface unit for fixing a periphery of the measuring portion during measurement.

The body-apparatus interface unit may include a fixing section for securing the periphery of the measuring portion, an expanding section for stretching the measuring portion by expanding the fixing section, a body-light reacting section for compressing the measuring portion into a predetermined thickness, the body-light reacting section having two optical windows for transmitting light, and a thickness adjusting section for adjusting a distance between the two optical windows.

The apparatus may further include a spectroscope for dividing the light into a predetermined wavelength band, which is sensitive to the body component, the concentration of which is to be measured, and effectively cancels an influence of interfering material, a storage unit for storing the signals processed by the signal processing unit, and a display unit for displaying the processing result of the signal processing unit.

The apparatus may further include a temperature adjusting section for maintaining the measuring portion at a constant temperature.

In the apparatus, the light of the predetermined wavelength may be in the near-infrared spectrum when the body component, the concentration of which is to be measured, is glucose.

The fixing section may be operable to remove tension around the measuring portion having the predetermined thickness and the expanding section may be operable to expand the measuring portion to minimize a restoring force generated in the measuring portion.

The fixing section may include a plurality of fixing members capable of fixing at least two positions of the measuring portion and the expanding section may expand the measuring portion by expanding the plurality of fixing members.

At least one of the above features and other advantages may be provided by a body-apparatus interface unit of a non-invasive body component measuring apparatus for measuring a concentration of a body component in a measuring portion of a living body, the body-apparatus interface unit including a fixing section for securing a periphery of the measuring portion, an expanding section for stretching the measuring portion by expanding the fixing section, a body-light reacting unit for compressing the measuring portion into a predetermined thickness, the body-light reacting unit having two optical windows for transmitting light, and a thickness adjusting section for adjusting a thickness of the expanded measuring portion.

The unit may further include a temperature adjusting section for maintaining the measuring portion at a constant temperature.

The unit may further include a support section for facilitating positioning of the measuring portion.

In the unit, the fixing section may include a plurality of fixing members capable of fixing at least two positions of the measuring portion and the expanding section may expand the measuring portion by expanding the plurality of fixing members.

The fixing section may be a disposable fixing device, including an upper cover having an upper window of a predetermined shape, a lower cover having a lower window of the predetermined shape, and a hooking section for securing a periphery of the measuring portion by inserting the periphery of the measuring portion, which is expanded by the expanding section, between the upper cover and the lower cover. Either one or both of the upper cover and the lower cover may be coated with an adhesive material attached to the measuring portion.

At least one of the above features and other advantages may be provided by a method of non-invasively measuring a concentration of a body component in a measuring portion of a living body, the method including adjusting a thickness of the measuring portion into a first thickness, removing tension around the measuring portion having the first thickness, measuring a first absorption spectrum from the measuring portion having the first thickness, adjusting the thickness of the measuring portion into a second thickness, measuring a second absorption spectrum from the measuring portion having the second thickness, establishing a statistical model about the body component using the first and second absorption spectra and an actually-measured concentration of the body component, and estimating the concentration of the body component using a difference absorption spectrum measured from the measuring portion using the statistical model.

The method may further include maintaining a periphery of the measuring portion having the first thickness at a constant temperature.

In the method, at least two positions of the measuring portion may be fixed prior to removing the tension around the measuring portion.

The method may further include expanding the measuring portion after removing the tension around the measuring portion.

In the method, when the thickness of the measuring portion is adjusted from the first thickness to the second thickness, a repulsive pressure of the measuring portion may be about 0.03 N/mm$^2$ or less.

BRIEF DESCRIPTION OF THE DRAWINGS

The above and other features and advantages of the present invention will become more apparent to those of ordinary skill in the art by describing in detail exemplary embodiments thereof with reference to the attached drawings in which.

DETAILED DESCRIPTION OF THE INVENTION

Figure 1:
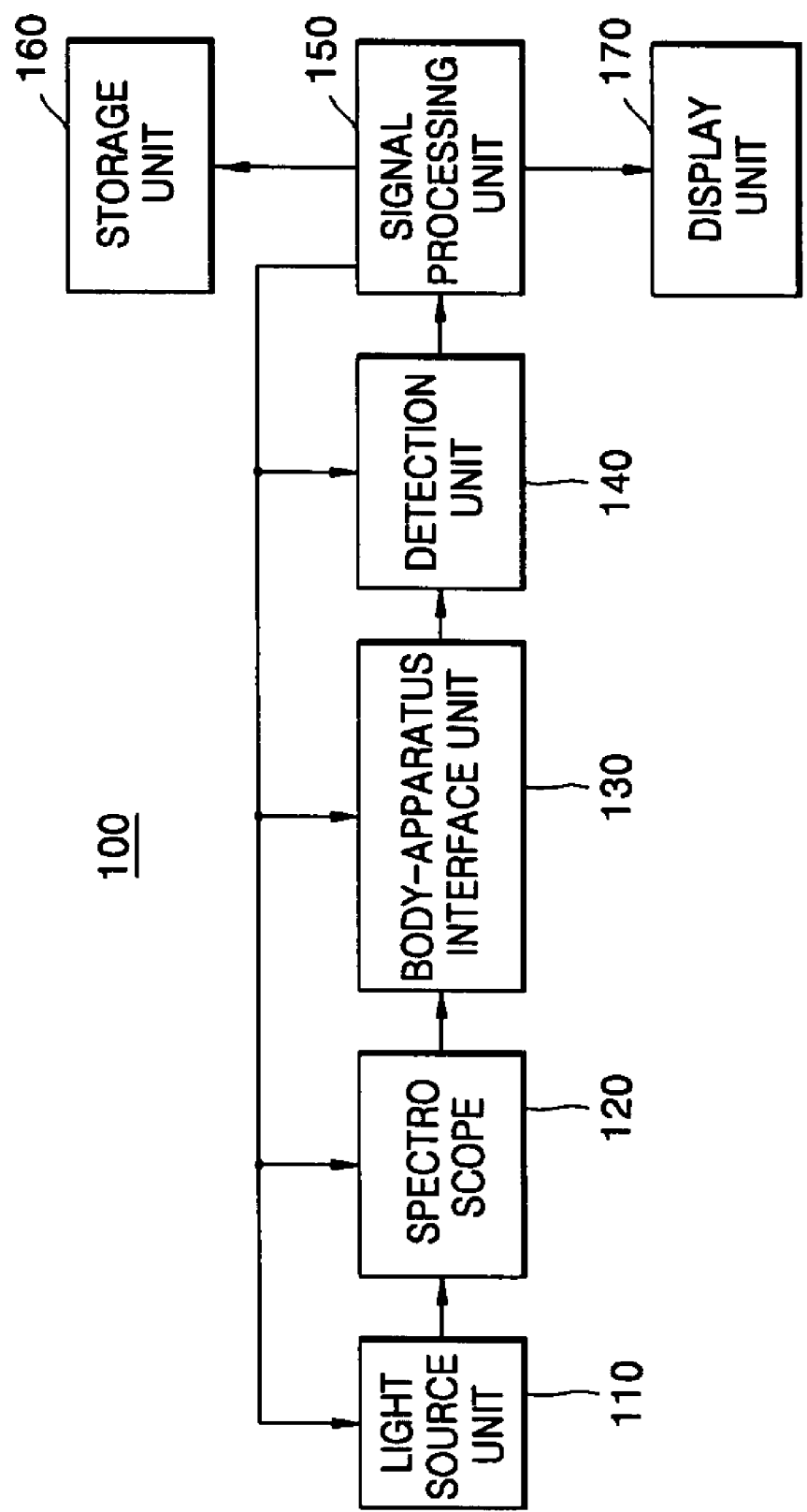
FIG. 1 is a block diagram illustrating a non-invasive body component measuring apparatus according to an exemplary embodiment of the present invention.

Korean Patent Application No. 2004-4407, filed on Jan. 20, 2004, in the Korean Intellectual Property Office, and entitled: "Non-Invasive Body Component Measuring Apparatus and Method," is incorporated by reference herein in its entirety.

The present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art. In the drawings, the thicknesses of layers and regions are exaggerated for clarity. Like reference numerals and characters indicate like elements throughout.

A human body consists of 73% water and 27% other components. One-third of the water is extracellular, and two-thirds of the water is intracellular. Of the extracellular water, three-quarters is interstitial fluid, and one-quarter is intravascular fluid. One blood component is blood sugar, which refers to a concentration of glucose in blood. The concentration of glucose contained in the blood flowing along a capillary vessel is similar to that of the interstitial fluid. The present invention involves a characteristic of glucose included in the interstitial fluid and the blood.

FIG. 1 is a block diagram illustrating a non-invasive body component measuring apparatus according to an exemplary embodiment of the present invention.

The non-invasive body component measuring apparatus 100 includes a light source unit 110 having a light source, such as a tungsten halogen lamp for generating light of a predetermined wavelength, and a light guide section for guiding the light generated from the light source onto a specific portion of tissue where a measurement is to be taken, i.e., a measuring portion, a spectroscope 120 for dividing the light from the light source unit 110 into a spectrum, a body-apparatus interface unit 130 for allowing the spectrum divided by the spectroscope 120 to pass through a sample, which is a specific portion of a human body, and to be sent to a detection unit 140, a signal processing unit 150, a storage unit 160, and a display unit 170.

Figure 2:
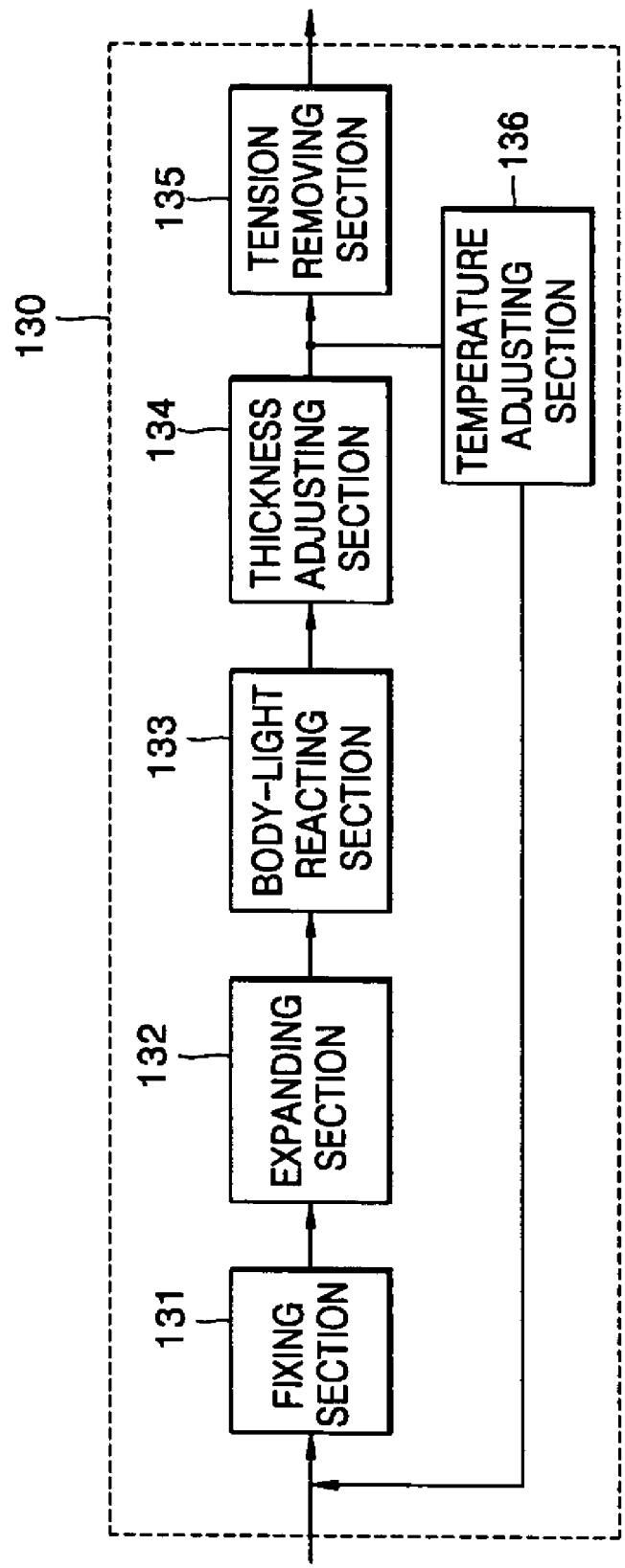
FIG. 2 is a block diagram illustrating a body-apparatus interface unit according to an exemplary embodiment of the present invention.

FIG. 2 is a block diagram illustrating an embodiment of the body-apparatus interface unit 130 shown in FIG. 1.

The body-apparatus interface unit 130 includes a temperature adjusting section 136 for adjusting a temperature of the measuring portion, a fixing section 131 for securing a measuring portion of a sample, such as a web between a thumb and an index finger, an expanding section 132 for expanding the measuring portion by pulling the fixing section 131, a body-light reacting section 133 for compressing the measuring portion into a predetermined thickness and having two optical windows for transmitting light, a thickness adjusting section 134 for adjusting a thickness of the measuring portion between the two optical windows, and a tension removing section 135 for removing the tension around the measuring portion.

Referring back to FIG. 1, the detection unit 140 detects an absorption spectrum from the measuring portion, which is fixed by the body-apparatus interface unit 130, and transmits the detected absorption spectrum to the signal processing unit 150. The signal processing unit 150 includes a program to be executed based on a statistical model for calculating the concentration of a body component.

Further, the signal processing unit 150 measures the absorption spectra, which are obtained by the detection unit 140, at the respective thicknesses of the specific soft tissue, obtains a difference absorption spectrum corresponding to the variation of thickness, and estimates the concentration of a specific body component corresponding to the difference absorption spectrum using the built-in program.

The storage unit 160 may store the processing result of the signal processing unit 150. The display unit 170 can display the concentration of the body component, e.g., glucose, as the processing result of the signal processing unit 150 or can display whether the measured data are normal by comparing the estimated concentration with data of a normal person. In addition, the display unit 170 may display simple medical instructions in accordance with the measured data.

Figure 3A:
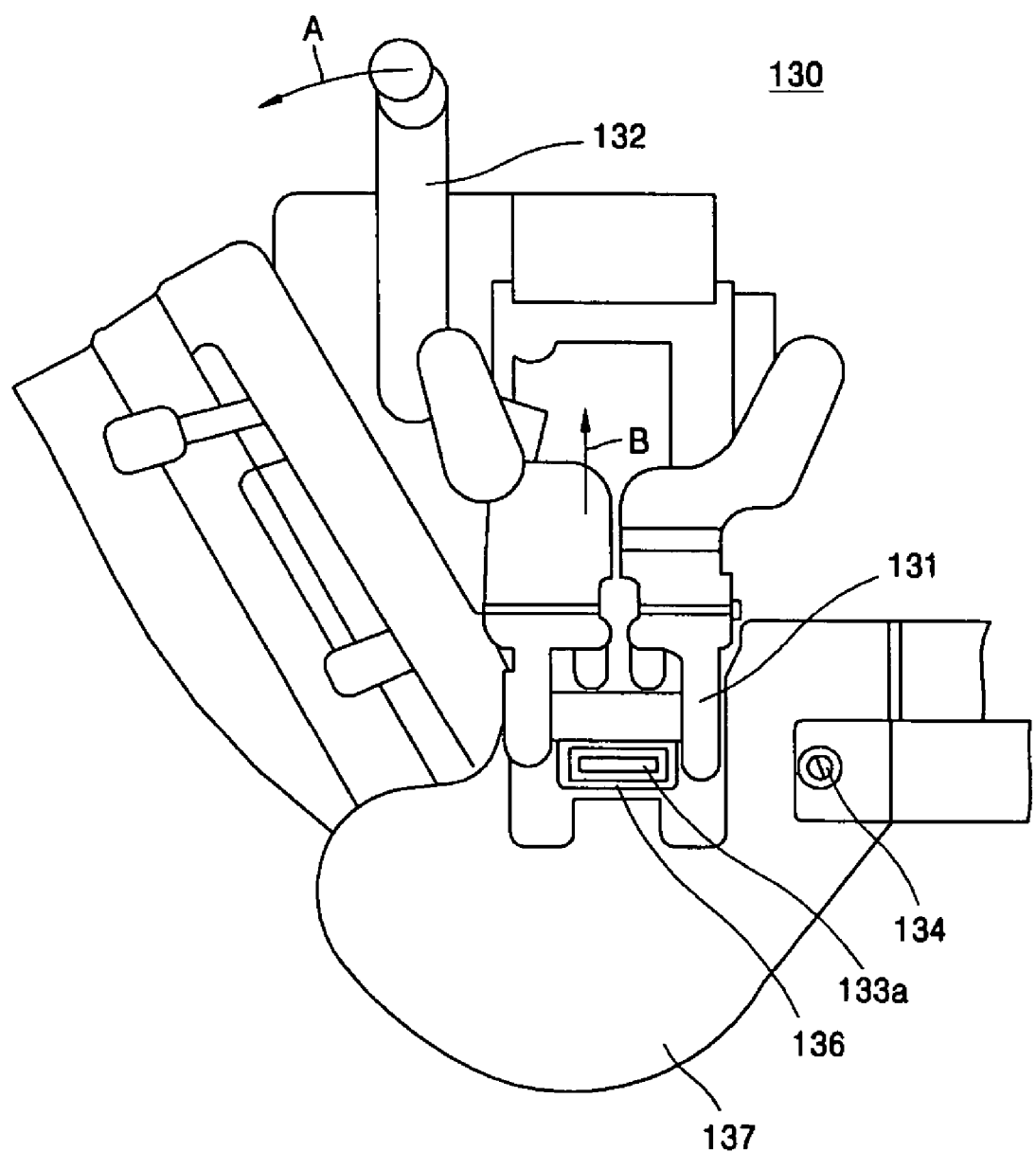
FIGS. 3A and 3B illustrate a plan view and a perspective view of a body-apparatus interface unit including a thickness adjusting section included in the non-invasive body component measuring apparatus shown in FIGS. 1 and 2, respectively.
Figure 3B:
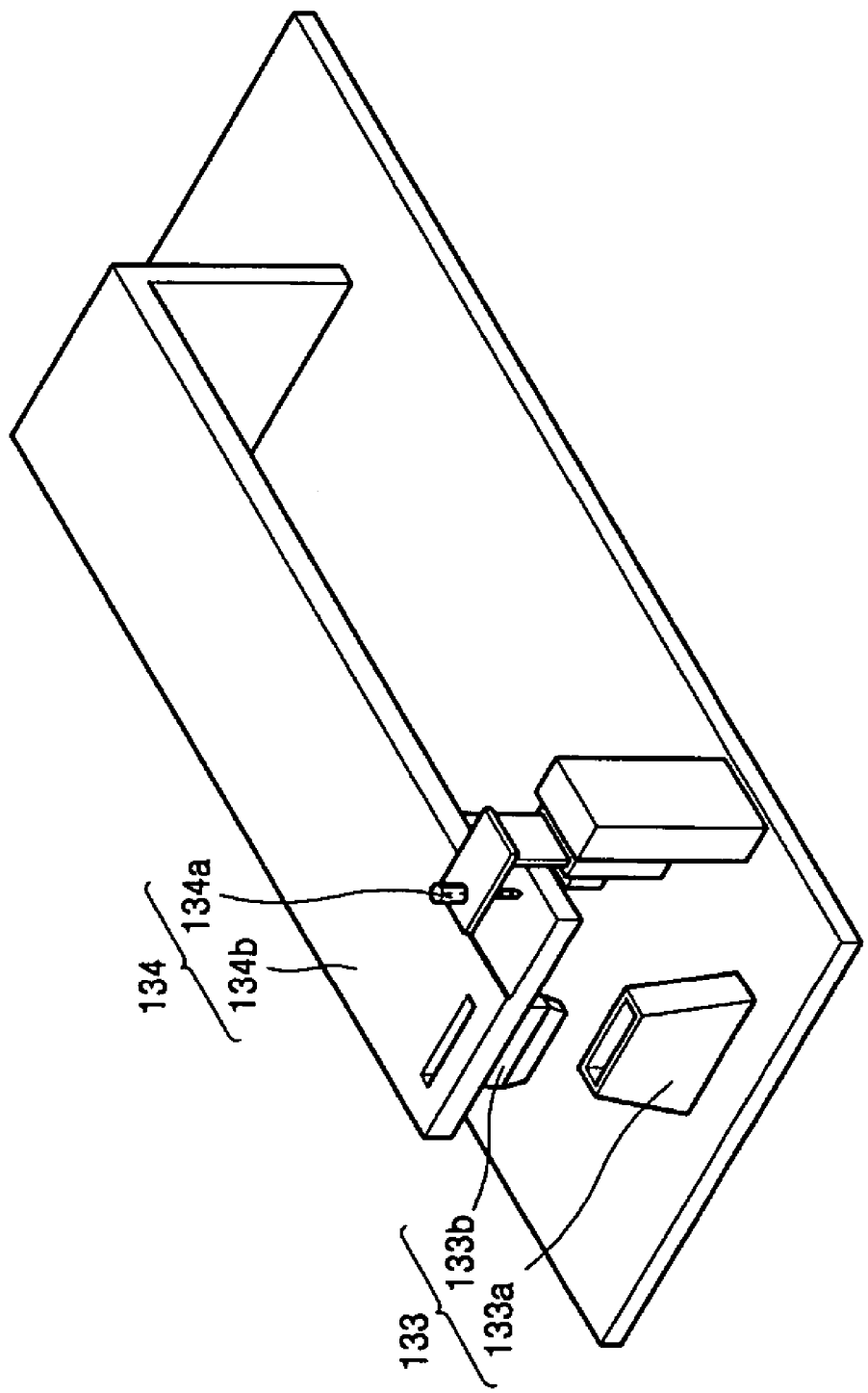
Figure 3C:
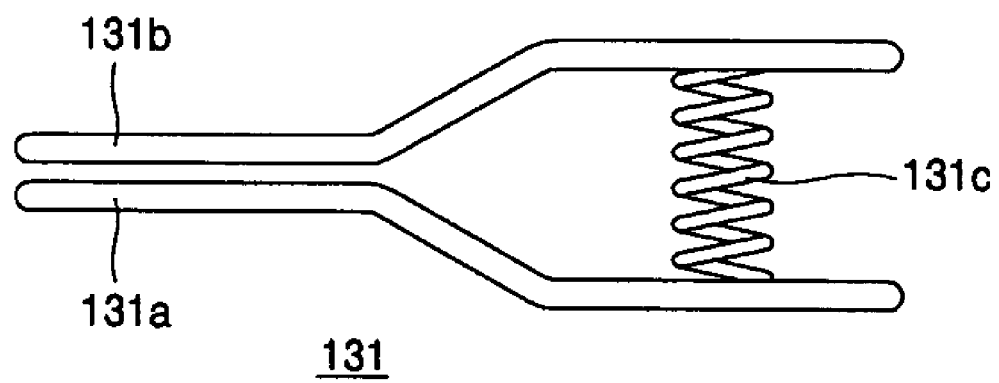
FIGS. 3C and 3D illustrate side views of a fixing section according to an exemplary embodiment of the present invention.
Figure 3D:
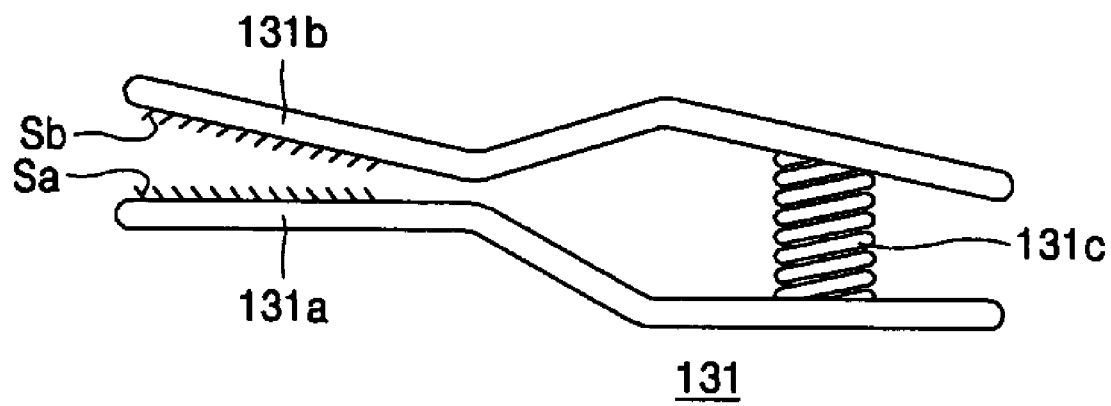

FIGS. 3A and 3B illustrate a plan view and a perspective view of the body-apparatus interface unit including a thickness adjusting section provided in the non-invasive body component measuring apparatus according to an exemplary embodiment of the present invention, respectively. FIGS. 3C and 3D illustrate side views of the fixing section according to an exemplary embodiment of the present invention.

Operations of the body-apparatus interface unit and the thickness adjusting section according to the present invention will be described with reference to FIGS. 3A through 3D.

First, a measuring portion is placed on a support section 137 and both ends of the measuring portion are then fixed with the fixing section 131. As shown in FIGS. 3C and 3D, the fixing section 131 may have a clip shape for fixing the measuring portion between an upper part 131b and a lower part 131a with a force of a spring 131c. Thereafter, by pulling the expanding section 132 in the arrow direction A, the fixing section 131 is moved in the arrow direction B.

Accordingly, the measuring portion fixed by the fixing section 131 is pulled and stretched widely. At this time, the measuring portion is placed on a first optical window 133a. The temperature adjusting section 136 is provided around the first optical window 133a, so that a portion of the body-apparatus interface section contacting the measuring portion is maintained at a constant temperature. Although not shown in FIG. 3A, light generated from a light source unit 110 and divided by a spectroscope 120 is emitted to the measuring portion of a body through the first optical window 133a.

FIG. 3B shows the body-light reacting section 133 and the thickness adjusting section 134. As shown in FIG. 3B, the thickness adjusting section 134 includes a micrometer 134a fitted to a cover support 134b having one end to which a second optical window 133b is fixed, and adjusts the thickness of the measuring portion by allowing the micrometer 134a to move the cover support 134b up and down. However, the present invention is not limited to this structure, but the thickness of the measuring portion may be adjusted by varying the pressure to the measuring portion. Although not shown in FIG. 3B for the purpose of convenience, the expanding section 132 and the fixing section 131 shown in FIG. 3A exist below the cover support 134b. That is, the cover support 134b passes over across the expanding portion 132 and the fixing portion 131 of FIG. 3A. In FIG. 3A, the cover support 134b is omitted in order to specifically show the expanding section 132 and the fixing section 131. For example, a hinge is connected one end of the cover support 134b, so that the cover support 134b can rotate up and down. Therefore, only during operation of the measuring apparatus, the cover support 134b is positioned above the expanding section 132 and the fixing section 131, and in the other cases, the cover support 134b can be pulled back.

When the cover support 134b rotates and is positioned above the expanding section 132 and the fixing section 131, the second optical window 133b fixed to one end of the cover support 134b opposes the first optical window shown in FIG. 3A. The first and second optical windows 133a and 133b constitute the body-light reacting section 133. The light emitted through the first optical window 133a and passing through the measuring portion is input to the second optical window 133b. The second optical window 133b is connected to the detecting unit 140, and the light input to the second optical window 133b is transferred to the detecting unit 140.

On the other hand, when it is intended to remove tension around the measuring portion, as shown in FIG. 3D, the upper part 131b of the fixing section 131 is fixed. Therefore, the tension removing section 135 may have a latch shape for fixing the upper part 131b of the fixing section 131 having a clip shape to a specific position. At this time, opposing surfaces Sb and Sa may be coated with an adhesive material, so that the measuring portion between the upper part 131b and the lower part 131a does not depart from the fixing section 131. Here, the adhesive material may be a disposable sticker, etc.

Figure 4A:
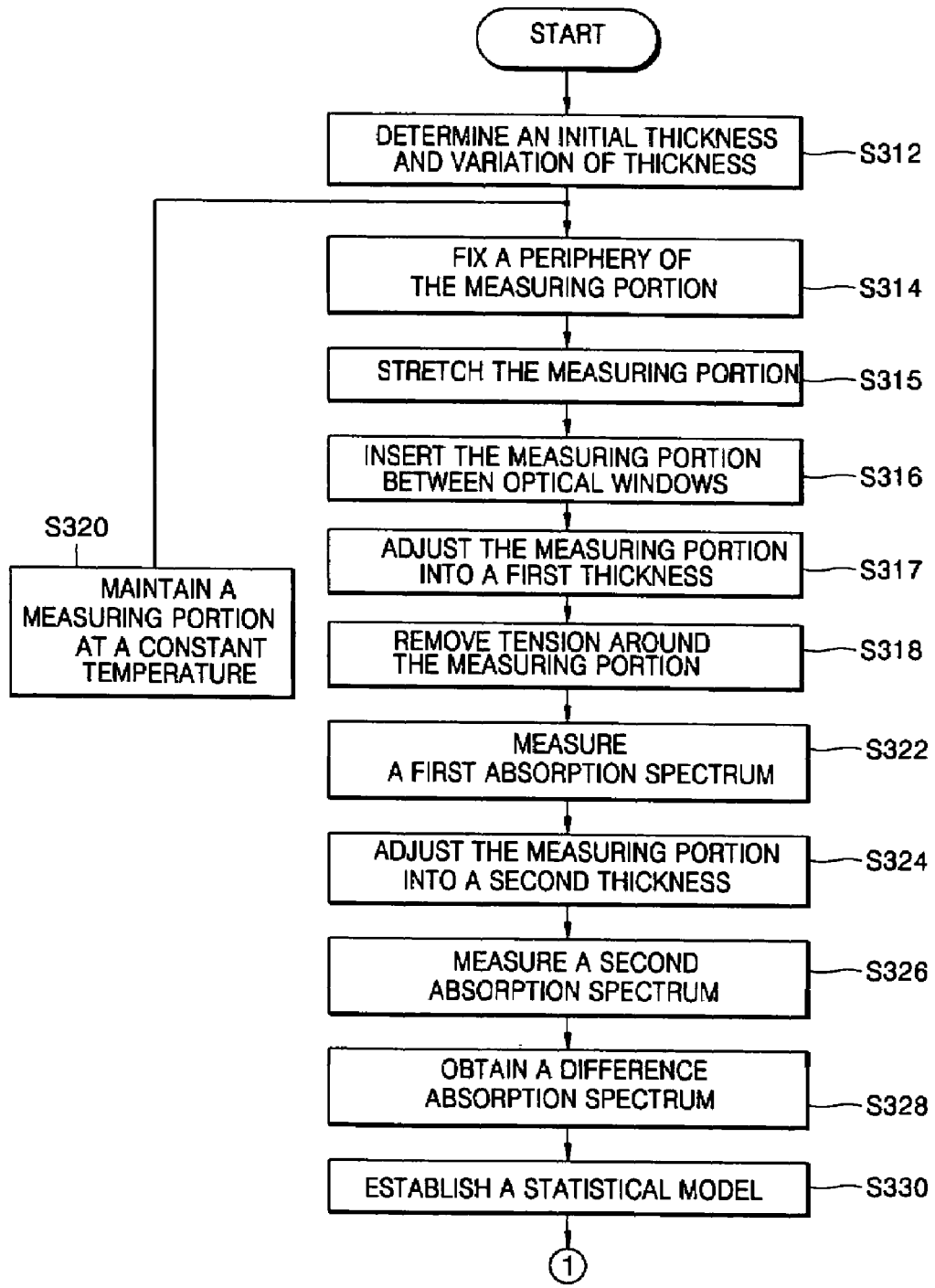
FIGS. 4A and 4B are flowcharts illustrating a non-invasive body component measuring method according to an exemplary embodiment of the present invention.
Figure 4B:
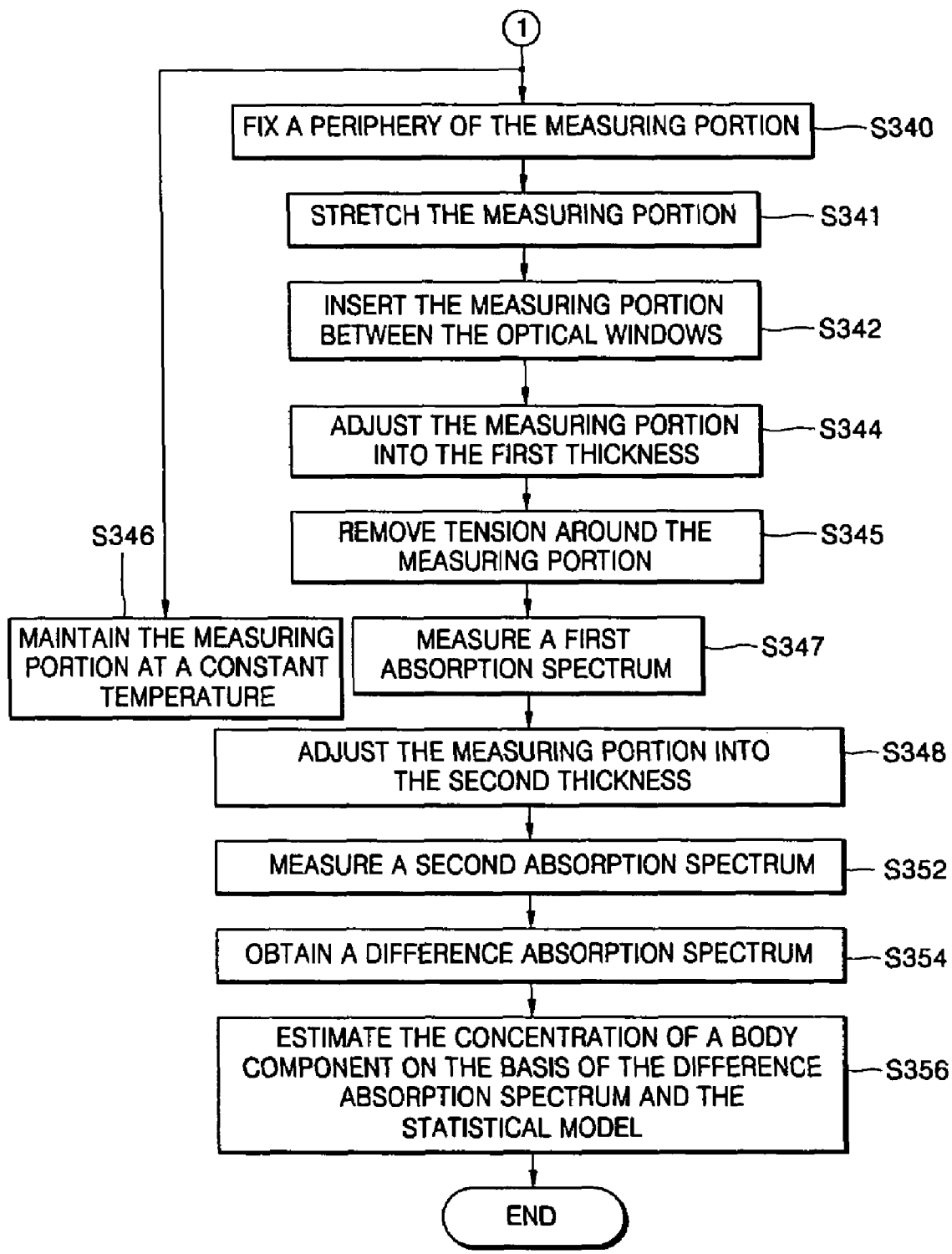

FIGS. 4A and 4B are flowcharts illustrating a non-invasive body component measuring method according to an exemplary embodiment of the present invention.

Operations for establishing a statistical model are shown in FIG. 4A. In operation S312, an initial thickness of a measuring portion, which is a specific soft tissue of a living body such as a human body, is determined. The measuring portion is the specific soft tissue of the living body where the measurement is to be taken. For example, the initial thickness can be determined from a thickness corresponding to application of an excessive pressure to the measuring portion. The excessive pressure that is measured varies depending on the person, i.e., the subject, and the location of the measuring portion on the body. Thus, the initial thickness varies depending on person and location of the measuring portion. The variation of the thickness should then be determined such that a difference in repulsive pressure of the biological tissue between two thicknesses, i.e., a first thickness and a second thickness, is about 0.03 N/mm$^2$ or less.

In operation S320, the body-apparatus interface unit contacting the measuring portion is maintained at a constant temperature.

Subsequently, in operation S314, several positions of the measuring portion are fixed with clips to secure the measuring portion. According to an exemplary embodiment of the present invention, the several positions include at least two positions and it is preferable that three or four positions are fixed.

In operation S315, the measuring portion is stretched, e.g., widely, by drawing and expanding the fixed positions of the measuring portion. At that time, according to an exemplary embodiment of the present invention, by selecting at least three positions to be fixed by the fixing section, the measuring portion can be stretched.

Then, in operation S316, the measuring portion is inserted between two optical windows.

Subsequently, in operation S317, the measuring portion, which is stretched, is adjusted into a first thickness. The initial thickness of the measuring portion may be adjusted into the first thickness by the thickness adjusting section.

In operation S318, the tension of the soft tissue fixed with the clips is removed. The stretched measuring portion may be relaxed to minimize the restoring force generated when the measuring portion is stretched.

Next, in operation S322, the first absorption spectrum is measured by applying light having a predetermined wavelength band having specificity of a specific body component to the measuring portion and receiving the light reflected or transmitted by the measuring portion. Here, the measuring portion may be located at various parts of the body such as a finger web, an earflap, an ear lobe, a nose, a lip, and the like. The wavelength band of the light applied to the measuring portion varies depending on the body component to be measured. For example, when the body component is glucose, the wavelength band preferably includes about 1,100 nm to 2,500 nm.

In operation S324, the thickness of the measuring portion is then adjusted from the first thickness to a second thickness. In operation S326, a second absorption spectrum is measured by applying light of the predetermined wavelength band to the measuring portion, of which the thickness is adjusted into the second thickness, and receiving the light reflected or transmitted by the measuring portion.

Subsequently, in operation S328, a difference absorption spectrum between the first and second absorption spectra obtained in operations S322 and S326 is obtained. From the difference absorption spectrum, spectra due to water or other components, which are prevention or interference factors in measurement of a body component, are removed. That is, since errors due to factors not relating to a specific body component of the sample are included in both the first and second absorption spectra, the errors can be removed by performing subtraction on the first and second absorption spectra. For example, a temperature of a sample, hydration of a tissue, presence of bone, cartilage, or collagen, and the like may influence the optical measurement of a body component, but are factors not directly relating to the body component itself. Therefore, by performing subtraction on the first and second absorption spectra, errors due to these factors can be removed.

Thus, in operation S330, a statistical model is established by performing a multi-variation statistical analysis to pairs of difference absorption spectra and actually-measured concentrations obtained by repeating operations S312 through S328 for each actually-measured concentration obtained from direct collection of blood from a specific person.

The statistical model for a specific person established in operation S330 is stored in the signal processing unit 150 of the non-invasive body component measuring apparatus 100.

FIG. 4B illustrates operations S340 to S356, which are performed to estimate a body component.

After establishing the statistical model in operation S332, in operation S346, the body-apparatus interface unit contacting the measuring portion is maintained at a constant temperature.

Subsequently, in operation S340, several positions of the measuring portion are fixed with clips to secure the measuring portion.

In operation S341, the measuring portion is stretched by drawing and expanding the fixed positions of the measuring portion.

Then, in operation S342, the measuring portion is inserted between two optical windows.

Subsequently, in operation S344, the measuring portion is adjusted into the first thickness. In operation S345, the tension of the measuring portion, which is fixed by the clips and stretched by the expanding section, is removed. Then, in operation S346, the first absorption spectrum is measured.

Subsequently, in operation S348, the measuring portion is adjusted into the second thickness. In operation S352, a second absorption spectrum is measured from the measuring portion having the second thickness. In operation S354, the difference absorption spectrum is obtained from the first and second absorption spectra.

Finally, in operation S356, the concentration of the relevant body component is estimated based on the difference absorption spectrum obtained in operation S354 and the statistical model obtained in operation S332.

When the wavelength area of the light source is varied, the non-invasive body component measuring method described in FIGS. 4A and 4B may be applied to obtain concentrations of hemoglobin, cholesterol, medications, and other analytic reagents, in addition to glucose.

Figure 5A:
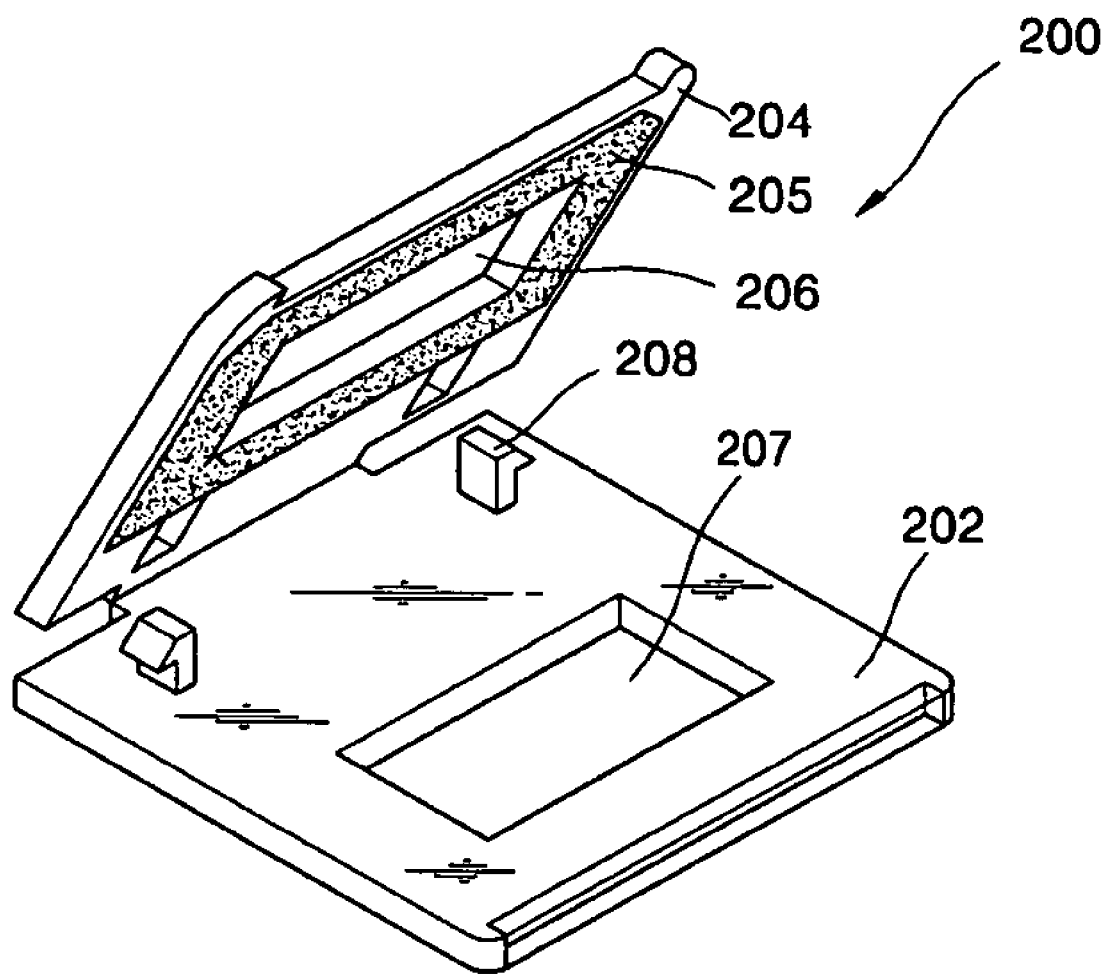
FIGS. 5A and 5B illustrate a perspective view and a plan view, respectively, of a disposable fixing device and a detachable expanding device for fixing an expanded measuring portion in the body-apparatus interface unit provided in a non-invasive body component measuring apparatus according to another exemplary embodiment of the present invention.

The exemplarily body-apparatus interface unit 130 shown in FIGS. 3A through 3D includes the fixing section 131 for fixing the measuring portion, the expanding section 132 for stretching the measuring portion, the body-light reacting section 133 for allowing light to be applied to the measuring portion, and the thickness adjusting section 134 for adjusting the thickness of the measuring portion, all of which are unified in a single unit. However, in this case, there are disadvantages that the size of the entire system is increased and a patient fixes his measuring portion to one position for a long time. In addition, since measuring portions of several patients are measured successively using the same fixing section, there is a sanitary problem. Therefore, if the fixing section is made disposable, the sanitary problem can be solved, and if the expanding section is detached from the entire system, the size of the entire system can be reduced. FIG. 5A illustrates a perspective view of a disposable fixing device designed for such needs and FIG. 5B illustrates a plan view of a detachable expanding device.

Figure 6:
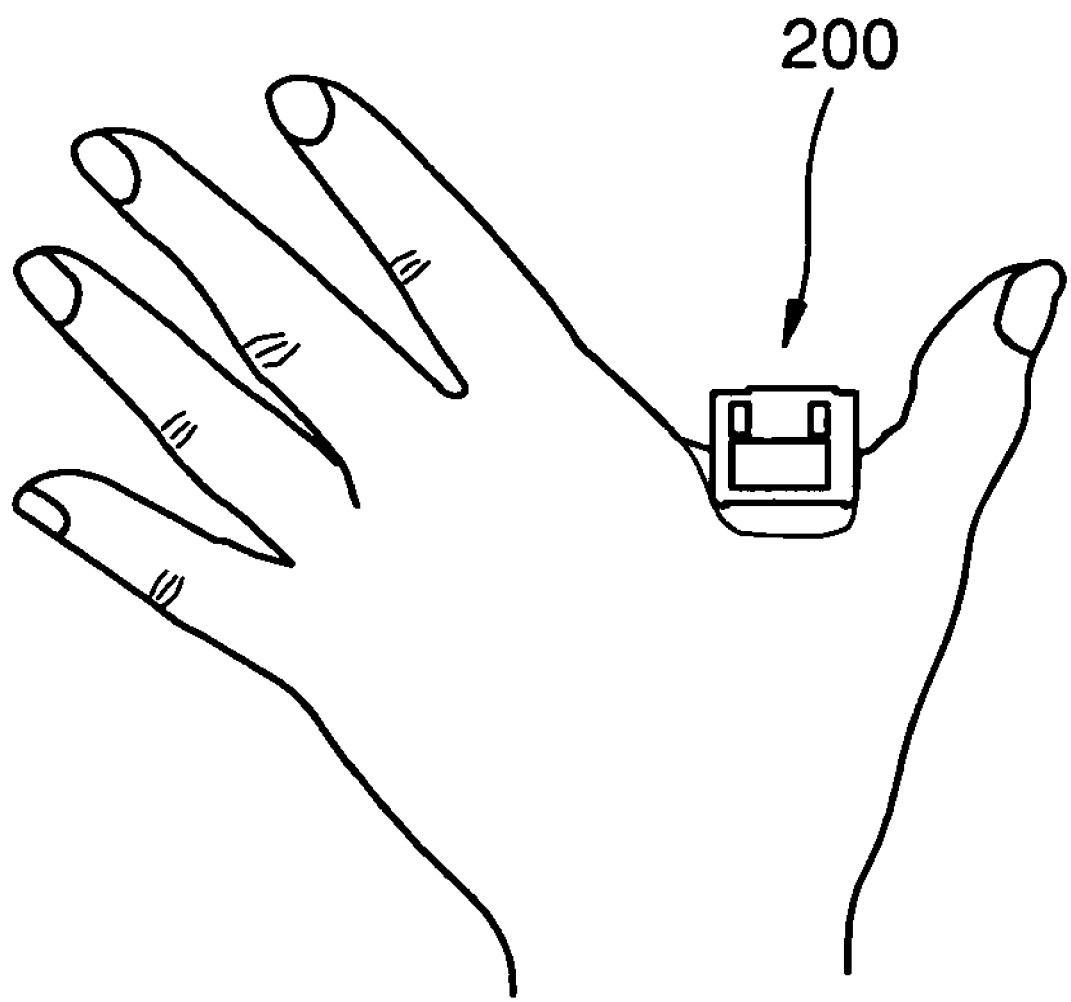
FIG. 6 is a diagram illustrating an exemplary application of the disposable fixing device shown in FIGS. 5A and 5B to a web between a thumb and an index finger of a human body.

FIG. 6 is a diagram illustrating a state where the disposable fixing device 200 shown in FIG. 5A is applied to a web between a thumb and an index finger of a human body.

Figure 5B:
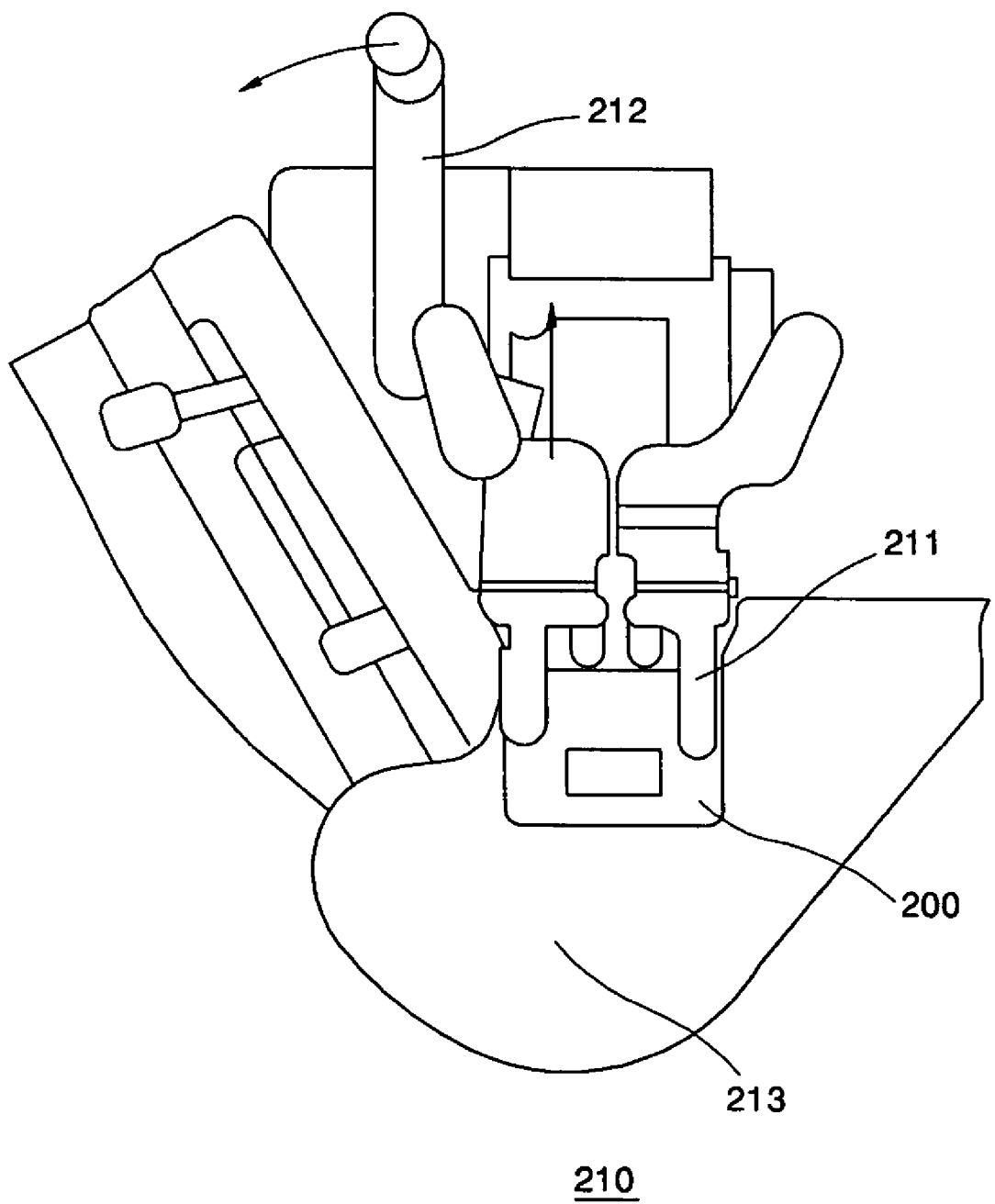

Referring to FIGS. 5A, 5B and 6, the disposable fixing device 200 includes an upper cover 204 having an upper window 206 of a predetermined shape, a lower cover 202 having a lower window 207 corresponding to the upper window 206, and a hooking section 208 fixing the lower cover 202 to the upper cover 204. The upper cover 204 may be coated with an adhesive material 205 for adhering to the measuring portion. For example, the adhesive material 205 may be a sticker. In addition, the lower cover 202 may be coated with the adhesive material 205.

Now, a case where the disposable fixing device 200 is coupled to the body-apparatus interface unit for operation will be described in detail.

The measuring portion of a specific soft tissue of a human body is fixed to the disposable fixing device 200 by inserting the specific soft tissue between the upper cover 204 having the upper window 206 and the lower cover 202 having the lower window 207 and securing the lower cover 202 to the upper cover 204 using the hooking section 208.

As shown in FIG. 5B, first, the disposable fixing device 200 is inserted into the detachable expanding device 210 with the disposable fixing device 200 opened, and several positions of the measuring portion are fixed with clips 211 to stretch the measuring portion. Next, the measuring portion is stretched by drawing and expanding the fixed positions of the measuring portion using the expanding section 212. Next, by coupling the lower cover 202 and the upper cover 204 of the disposable fixing device 200 together, the measuring portion of the specific soft tissue is fixed. Thereafter, the disposable fixing device 200 is detached from the detachable expanding device 210, and, as shown in FIG. 6, a hand, to which the disposable fixing device 200 is coupled, is then inserted between additional optical windows for measuring a spectrum. The structure of the optical windows is the same as shown in FIG. 3B, and the thickness adjusting section is unified to the optical windows. Support 213 conveniently positions the measuring portion.

In an exemplary embodiment of the present invention, the disposable fixing device 200, to which the measuring portions is fixed, is coupled to the optical windows. Thereafter, by vertically moving the micrometer of the thickness adjusting section, the measuring portion can be adjusted into the first thickness.

Subsequently, the hooking section 208 of the disposable fixing device 200 is unlocked, thereby removing the tension around the measuring portion. In this case, since the upper cover 204 may be coated with the adhesive material 205, the measuring portion is still fixed to the disposable fixing device 200. At that time, according to an exemplary embodiment of the present invention, a temperature adjusting section including a Peltier device or a wire capable of generating heat may be further provided in the disposable fixing device 200.

The subsequent operations thereto are similar to those of the exemplary embodiment of the present invention described with reference to FIGS. 1 to 4B, and thus descriptions thereof will not be repeated.

As described above, according to the present invention, when a concentration of a body component is estimated on the basis of a difference absorption spectrum and a statistical model, it is possible to obtain a spectrum from a specific soft tissue while securing the specific soft tissue by fixing a periphery of the specific soft tissue during the measurement.

Therefore, according to the present invention, by stably adjusting the specific soft tissue, it is possible to enhance the reproducibility of absorbance and to enhance the accuracy in measurement of a body component.

Exemplary embodiments of the present invention have been disclosed herein, and although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A non-invasive body component measuring apparatus for measuring a concentration of a body component in a measuring portion of a living body, the apparatus comprising:
   a light source unit for generating light of a predetermined wavelength;
   a spectroscope for dividing the light into a predetermined wavelength band and for applying the light onto the measuring portion;
   a detection unit for detecting light reflected or transmitted by the measuring portion and for converting the detected light into an electrical signal;
   a signal processing unit for processing the electrical signal; and
   a body-apparatus interface unit for fixing a periphery of the measuring portion during measurement, wherein the body-apparatus interface unit includes:
   a fixing section for securing the periphery of the measuring portion;
   an expanding section for stretching the measuring portion by expanding the fixing section;
   a body-light reacting section for compressing the measuring portion into a predetermined thickness, the body-light reacting section having two optical windows for transmitting light; and
   a thickness adjusting section for adjusting a distance between the two optical windows.

2. The apparatus as claimed in claim 1, further comprising:
   a storage unit for storing the signals processed by the signal processing unit; and
   a display unit for displaying the processing result of the signal processing unit,
   wherein the spectroscope is sensitive to the body component, the concentration of which is to be measured, and effectively cancels an influence of interfering materials.

3. The apparatus as claimed in claim 1, further comprising a temperature adjusting section for maintaining the measuring portion at a constant temperature.

4. The apparatus as claimed in claim 1, wherein the light of the predetermined wavelength is in a near-infrared spectrum when the body component, the concentration of which is to be measured, is glucose.

5. The apparatus as claimed in claim 1, wherein the fixing section is operable to remove tension around the measuring portion having the predetermined thickness and the expanding section is operable to expand the measuring portion to minimize a restoring force generated in the measuring portion.

6. The apparatus as claimed in claim 1, wherein the fixing section includes a plurality of fixing members capable of fixing at least two positions of the measuring portion and the expanding section expands the measuring portion by expanding the plurality of fixing members.

7. A body-apparatus interface unit of a non-invasive body component measuring apparatus for measuring a concentration of a body component in a measuring portion of a living body, the body-apparatus interface unit comprising:
    a fixing section for securing a periphery of the measuring portion;
    an expanding section for stretching the measuring portion by expanding the fixing section;
    a body-light reacting unit for compressing the measuring portion into a predetermined thickness, the body-light reacting unit having two optical windows for transmitting light; and
    a thickness adjusting section for adjusting a thickness of the expanded measuring portion.

8. The body-apparatus interface unit as claimed in claim 7, further comprising a temperature adjusting section for maintaining the measuring portion at a constant temperature.

9. The body-apparatus interface unit as claimed in claim 7, further comprising a support section for facilitating positioning of the measuring portion.

10. The body-apparatus interface unit as claimed in claim 7, wherein the fixing section includes a plurality of fixing members capable of fixing at least two positions of the measuring portion and the expanding section expands the measuring portion by expanding the plurality of fixing members.

11. The body-apparatus interface unit as claimed in claim 7, wherein the fixing section is a disposable fixing device including:
    an upper cover having an upper window of a predetermined shape;
    a lower cover having a lower window of the predetermined shape; and
    a hooking section for securing a periphery of the measuring portion by inserting the periphery of the measuring portion, which is expanded by the expanding section, between the upper cover and the lower cover.

12. The body-apparatus interface unit as claimed in claim 11, wherein either one or both of the upper cover and the lower cover is coated with an adhesive material.

13. A method of non-invasively measuring a concentration of a body component in a measuring portion of a living body, the method comprising:
    adjusting a thickness of the measuring portion into a first thickness;
    removing tension around the measuring portion having the first thickness;
    measuring a first absorption spectrum from the measuring portion having the first thickness;
    adjusting the thickness of the measuring portion into a second thickness;
    measuring a second absorption spectrum from the measuring portion having the second thickness;
    establishing a multivariate statistical model about the body component using the first and second absorption spectra and an actually-measured concentration of the body component; and
    estimating the concentration of the body component using a difference absorption spectrum measured from the measuring portion using the statistical model.

14. The method as claimed in claim 13, further comprising maintaining a periphery of the measuring portion having the first thickness at a constant temperature.

15. The method as claimed in claim 13, wherein at least two positions of the measuring portion are fixed prior to removing the tension around the measuring portion.

16. The method as claimed in claim 13, further comprising expanding the measuring portion after removing the tension around the measuring portion.

17. The method as claimed in claim 13, wherein when adjusting the thickness of the measuring portion from the first thickness to the second thickness, a difference in repulsive pressure of the measuring portion is about 0.03 $N/mm_2$ or less.

18. The method as claimed in claim 13, wherein the multivariate statistical model is established by performing a multi-variational statistical analysis to pairs of difference absorption spectra and actually measured concentrations.

19. The method as claimed in claim 18, wherein the pairs of difference absorption spectra and actually measured concentrations are obtained by repeating operations for each actually measured concentration obtained from direct collection of blood from a specific person.

* * * * *